(12) United States Patent
Gore et al.

(10) Patent No.: US 9,181,268 B2
(45) Date of Patent: Nov. 10, 2015

(54) ANHYDRATE OF TIOTROPIUM BROMIDE

(71) Applicant: GENERICS [UK] LIMITED, Hertfordshire (GB)

(72) Inventors: Vinayak Govind Gore, Maharashtra (IN); Bindu Manojkumar, Maharashtra (IN); Dattatraya Shinde, Maharashtra (IN); Dattatrey Kokane, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 0 days.

(21) Appl. No.: 14/246,291

(22) Filed: Apr. 7, 2014

(65) Prior Publication Data

US 2014/0249175 A1 Sep. 4, 2014
US 2015/0051241 A9 Feb. 19, 2015

Related U.S. Application Data

(62) Division of application No. 13/386,550, filed as application No. PCT/GB2010/051310 on Aug. 6, 2010, now Pat. No. 8,697,719.

(30) Foreign Application Priority Data

Aug. 7, 2009 (IN) .......................... 1048/KOL/2009

(51) Int. Cl.
*C07D 491/18* (2006.01)
*C07D 451/10* (2006.01)

(52) U.S. Cl.
CPC ............ *C07D 491/18* (2013.01); *C07D 451/10* (2013.01)

(58) Field of Classification Search
None
See application file for complete search history.

(56) References Cited

U.S. PATENT DOCUMENTS

| | | | |
|---|---|---|---|
| 5,610,163 | A | 3/1997 | Banholzer et al. |
| 6,486,321 | B2 | 11/2002 | Banholzer et al. |
| 6,506,900 | B1 | 1/2003 | Banholzer et al. |
| 6,608,055 | B2 | 8/2003 | Sieger et al. |
| 6,610,849 | B2 | 8/2003 | Sobotta et al. |
| 6,747,153 | B2 | 6/2004 | Banholzer et al. |
| 6,747,154 | B2 | 6/2004 | Brandenburg et al. |
| 6,777,423 | B2 | 8/2004 | Banholzer et al. |
| 7,662,963 | B2 | 2/2010 | Busolli et al. |
| 2002/0133010 | A1 | 9/2002 | Banholzer et al. |
| 2004/0242622 | A1 | 12/2004 | Mammen et al. |
| 2005/0143410 | A1 | 6/2005 | Pfrengle et al. |
| 2007/0027320 | A1 | 2/2007 | Brandenburg et al. |
| 2007/0092453 | A1 | 4/2007 | Pop et al. |
| 2007/0167480 | A1 | 7/2007 | Volonte et al. |
| 2007/0225314 | A1 | 9/2007 | Diulgheroff et al. |
| 2008/0051582 | A1 | 2/2008 | Busolli et al. |

FOREIGN PATENT DOCUMENTS

| | | |
|---|---|---|
| AU | 1990064318 | 10/1994 |
| AU | 20022361218 | 7/2003 |
| CA | 2471755 | 7/2003 |
| CA | 2616222 | 7/2006 |
| CN | 1634921 | 7/2005 |
| CN | 100 410 254 | 8/2008 |
| EP | 0 418 716 | 3/1991 |
| JP | H05502438 | 4/1993 |
| JP | 2005519890 | 7/2005 |
| JP | 2007501862 | 2/2007 |
| WO | WO 02/30928 | 4/2002 |
| WO | WO 03/057694 | 7/2003 |
| WO | WO 2005/042527 | 5/2005 |
| WO | WO 2006/076222 | 7/2006 |
| WO | WO 2006/117300 | 11/2006 |
| WO | WO 2006117299 | 11/2006 |
| WO | WO 2007/012626 | 2/2007 |
| WO | WO 2007/075838 | 7/2007 |
| WO | WO 2007/075858 | 7/2007 |
| WO | WO 2008/008376 | 1/2008 |
| WO | WO 2008/089852 | 7/2008 |
| WO | WO 2008101591 | 8/2008 |
| WO | WO 2008/104955 | 9/2008 |
| WO | WO 2009/087419 | 7/2009 |
| WO | WO 2011/015882 | 2/2011 |
| WO | WO 2011/015883 | 2/2011 |
| WO | WO 2011/015884 | 2/2011 |
| WO | WO 2011/095800 | 8/2011 |

OTHER PUBLICATIONS

Ding, et al., Journal of Chromatographic Science, vol. 46, 2008, pp. 445-449.
Indian Pharmacopeia, vol. 3, "Tiotropium Bromide Monograph", 2007, p. 1812.
International Search Report PCT/GB2010/051310 dated Dec. 7, 2011 (6 pgs.).
IP.Com Journal, Jun. 17, 2009, 7 pages, (XP013132381).
IP.Com Journal, Nov. 30, 2006, 3 pages (XP013116939).
Wang, et al., Rapid Communications in Mass Spectrometry, No. 21, 2007, pp. 1755-1758.
Neuman, "Reactions of Haloalkanes, Alcohols, and Amines. Nucleophilic Substitution", from Organic Chemistry, Chapter 7, 1992, pp. 0-71.
The Chemical Society of Japan, Encyclopedia of Experimental Chemistry, 4th edition, vol. 1, Basic Operation I, Marusen, 1990, pp. 184-186.

*Primary Examiner* — Timothy R Rozof
(74) *Attorney, Agent, or Firm* — Arnold Krumholz (Lerner David)

(57) ABSTRACT

The present invention relates to a novel form of anhydrous tiotropium bromide, processes for the preparation of anhydrous tiotropium bromide, pharmaceutical compositions comprising anhydrous tiotropium bromide and uses of the compositions.

5 Claims, 3 Drawing Sheets

ANHYDRATE OF TIOTROPIUM BROMIDE

CROSS-REFERENCE TO RELATED APPLICATIONS

This application is a Divisional of U.S. application Ser. No. 13/386,550, filed Mar. 6, 2012, which is a 371 National Stage Application of International Application PCT/GB2010/051310, filed Aug. 6, 2010, which claims foreign priority to Indian patent application 1048/KOL/2009, filed Aug. 7, 2009, the contents of which are incorporated herein in their entirety.

FIELD OF THE INVENTION

The present invention relates to a novel form of anhydrous tiotropium bromide, processes for the preparation of anhydrous tiotropium bromide, pharmaceutical compositions comprising anhydrous tiotropium bromide and uses of the compositions.

BACKGROUND OF THE INVENTION

Tiotropium bromide (1), first disclosed in EP0418716, is a highly effective anticholinergic agent with specificity for muscarinic receptors and it is presently approved for the treatment of respiratory disorders, such as asthma or chronic obstructive pulmonary disease (COPD), including chronic bronchitis and emphysema.

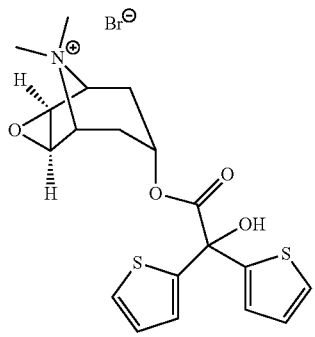

(1)

Tiotropium bromide is used in low (microgram) therapeutic doses and it is therefore particularly necessary to develop an industrial process for the commercial preparation of tiotropium bromide which ensures that the product is prepared not only in a high, economical yield but also with exceptional chemical and polymorphic purity.

The manufacturing process for many pharmaceuticals is hindered by the fact that the organic compound, which is the active ingredient, has handling difficulties during the manufacturing process and may impart undesirable properties to the final drug or dosage form. In addition it can be difficult to control the polymorphic form of the active pharmaceutical ingredient throughout the manufacturing process.

For pharmaceuticals in which the active ingredient can exist in more than one polymorphic or crystalline form, it is particularly important to ensure that the manufacturing process for the active ingredient affords a single, pure polymorph with a consistent level of polymorphic purity. If the manufacturing process leads to a polymorph with varying degrees of polymorphic purity and/or or where the process does not control polymorphic interconversion, serious problems in dissolution and/or bioavailability can result in the finished pharmaceutical composition comprising the active ingredient.

If crystalline forms are made with polymorphic impurities, this causes instability and it can accelerate significant interconversion to another polymorphic form. Therefore it is crucial to produce crystalline forms with very high polymorphic purity to avoid this interconversion.

A process for the preparation of tiotropium bromide was first reported in EP0418716. Tiotropium bromide monohydrate is disclosed in WO2002/30928 along with a method of its preparation by heating anhydrous tiotropium bromide in water in the presence of activated charcoal. In addition, there have been several subsequent disclosures of methods to prepare anhydrous tiotropium bromide from tiotropium bromide monohydrate or solvate.

A method of preparing anhydrous tiotropium bromide by heating tiotropium bromide monohydrate at 80-100° C. under vacuum is disclosed in U.S. Pat. No. 6,608,055. However, this method is not suitable for commercial manufacture as directly heating a solid at high temperature can lead to localized heating and inconsistent results.

Another method disclosed in U.S. Pat. No. 6,608,055 involves the conversion of tiotropium bromide monohydrate to anhydrous tiotropium bromide by storing over silica gel for 24 hours. However, this method is not amenable to commercial manufacturing.

An alternative method of preparing anhydrous tiotropium bromide, disclosed in WO2007/075858, involves heating tiotropium bromide methanolate or hemi-n-butanolate or hemi-acetate in an oven at 160° C. This requires very high temperatures and specific solvates as starting material.

Another method, disclosed in US2005/0143410, involves a process for converting tiotropium bromide monohydrate to anhydrous tiotropium bromide by boiling in water and adding ammonium fluoride. Alternatively, a crystallization method from methanol with seeding was reported.

A further method, disclosed in US2007/0092453, involves converting tiotropium bromide monohydrate to anhydrous tiotropium bromide by heating at 50° C. in a 1:1 N,N-dimethylacetamide/water mixture. Also reported are 14 different solvates of tiotropium bromide. However, this method in US2007/0092453 involves evaporation of high volumes of high boiling solvents at room temperature under a vacuum of 1 Kpa until crystals appear in the solution. The method is not particularly reproducible and as both N,N-dimethylacetamide and water are high boiling solvents (164° C. and 100° C. respectively), the removal of these solvents at room temperature requires high vacuum. Therefore removal of such volumes of N,N-dimethylacetamide and water at room temperature is practically very difficult for production on a commercial scale. In addition, the process is limited to tiotropium bromide monohydrate as starting material.

From the above prior art details, it can be observed that there is no direct method reported in the literature for preparing anhydrous tiotropium bromide. All the above processes reported for preparing anhydrous tiotropium bromide involve the preparation of either tiotropium bromide monohydrate or tiotropium bromide solvates as starting material to prepare anhydrous tiotropium bromide. This increases the number of steps and reduces the overall yield.

Hence it would be advantageous to have a direct method for preparing anhydrous tiotropium bromide which does not involve the preparation of either tiotropium bromide monohydrate or a tiotropium bromide solvate as starting material.

In addition, the processes described in the prior art typically require elevated temperatures and therefore can lead to impure products, since it has been observed that tiotropium bromide decomposes at higher temperatures generating scopine di-(2-thienyl)glycolate as an impurity. Consequently, there is a requirement for an additional purification step to afford pure anhydrous tiotropium bromide as it typically contains 0.1-0.5% of impurity scopine di-(2-thienyl)glycolate. In addition, the anhydrous tiotropium bromide formed in the prior art processes is not polymorphically pure.

In view of the importance acquired by tiotropium bromide for the treatment of respiratory disorders, there is a great need for developing an alternative, relatively simple, economical and commercially feasible process for the synthesis of tiotropium bromide crystalline forms with commercially acceptable yield, chemical purity and high polymorphic purity and polymorphic stability.

SUMMARY OF THE INVENTION

The inventors have observed that tiotropium bromide forms solvates with a wide range of solvents. Consequently, there is a need for developing a direct synthetic and purification method for anhydrous tiotropium bromide without using solvents which form solvates.

Therefore the present invention provides an efficient and simple process for the preparation of anhydrous tiotropium bromide directly without going through intermediate tiotropium bromide solvates or tiotropium bromide hydrates such as tiotropium bromide monohydrate.

The present invention also provides a chemically pure and polymorphically pure and stable form of anhydrous tiotropium bromide.

Surprisingly, the inventors have developed methods which involve solvents which do not form solvates for the direct preparation of anhydrous tiotropium bromide and its purification. The methods are short, very mild and convenient for commercial scale manufacture, particularly as elevated temperatures are avoided for reaction, purification and drying.

The process which has been developed involves the preparation of anhydrous tiotropium bromide directly from scopine di-(2-thienyl)glycolate using a very convenient, direct route, without the requirement of an extra synthetic step for initially forming and isolating a hydrate or solvate of tiotropium bromide.

In addition, the method affords a novel crystalline form of anhydrous tiotropium bromide which is chemically pure, polymorphically pure and polymorphically stable.

Accordingly, a first aspect of the present invention provides anhydrous tiotropium bromide having an XRPD pattern comprising at least three peaks (preferably at least four peaks, preferably at least five peaks, preferably at least six peaks, preferably at least seven peaks, preferably at least eight peaks, preferably at least nine peaks, preferably at least ten peaks, preferably at least twelve peaks, preferably at least fifteen peaks, preferably at least twenty peaks, preferably all twenty-two peaks) selected from peaks with 2θ angles of about 8.49, 11.38, 13.58, 14.24, 14.74, 16.01, 17.03, 17.93, 18.60, 19.15, 21.80, 22.62, 22.92, 23.29, 25.29, 25.57, 26.23, 27.29, 28.07, 28.61, 30.24 and 31.83±0.2 degrees. Preferably the first aspect of the present invention provides anhydrous tiotropium bromide with an XRPD spectrum substantially as shown in FIG. 1.

Preferably the anhydrous tiotropium bromide according to the first aspect of the present invention has a DSC spectrum with endothermic peaks at about 208° C.±2° C. and about 221° C.±2° C. Preferably the anhydrous tiotropium bromide according to the first aspect of the present invention has a DSC spectrum substantially as shown in FIG. 2.

Preferably the anhydrous tiotropium bromide according to the first aspect of the present invention has a TGA spectrum substantially as shown in FIG. 3.

Preferably the anhydrous tiotropium bromide according to the first aspect of the present invention comprises less than 5% of other polymorphic forms of tiotropium bromide, preferably less than 3%, preferably less than 2%, preferably less than 1%, preferably less than 0.5%, preferably less than 0.2%, preferably less than 0.1% (as measured by XRPD).

A second aspect of the present invention provides a process for the preparation of anhydrous tiotropium bromide, comprising the steps of:
(a) providing a solution of scopine di-(2-thienyl)glycolate and a first organic solvent;
(b) adding a solution of methyl bromide in a second organic solvent to the mixture from step (a) or vice versa;
(c) isolating anhydrous tiotropium bromide from the mixture obtained in step (b); and
(d) drying the isolated anhydrous tiotropium bromide.

Preferably the first and second organic solvents are not the same.

Preferably the first organic solvent is a ketone, preferably acetone, methyl ethyl ketone, methyl n-propyl ketone, methyl isopropyl ketone, methyl vinyl ketone, methyl n-butyl ketone, methyl isobutyl ketone, methyl tert-butyl ketone or diethyl ketone. Most preferably the first organic solvent is acetone.

Preferably the second organic solvent is a polar aprotic solvent, preferably acetonitrile.

In step (b), a solution of methyl bromide in a second organic solvent is added to the mixture from step (a) or alternatively the mixture from step (a) is added to a solution of methyl bromide in a second organic solvent. Preferably a solution of methyl bromide in a second organic solvent is added to the mixture from step (a).

Preferably the drying temperature is between about 40 to 80° C., more preferably about 60° C.

Preferably the process of the second aspect of the present invention comprises an additional process for further purifying the anhydrous tiotropium bromide.

Preferably the additional process for further purifying the anhydrous tiotropium bromide comprises:
(a) providing a solution of anhydrous tiotropium bromide and a third organic solvent;
(b) adding a fourth organic solvent as an anti-solvent to the solution from step (a);
(c) isolating purified anhydrous tiotropium bromide from the mixture obtained in step (b); and
(d) drying the isolated purified anhydrous tiotropium bromide.

Preferably the third organic solvent is a polar aprotic solvent, preferably dimethylsulfoxide, dimethylformamide or dimethylacetamide. Preferably the third organic solvent is dimethylsulfoxide.

Preferably the fourth organic solvent used as an anti-solvent is a ketone, preferably acetone, methyl ethyl ketone, methyl n-propyl ketone, methyl isopropyl ketone, methyl vinyl ketone, methyl n-butyl ketone, methyl isobutyl ketone, methyl tert-butyl ketone or diethyl ketone. Preferably the ketone is acetone.

Preferably the drying temperature used in the additional process for further purifying the anhydrous tiotropium bromide is between about 40 to 80° C. Preferably the drying temperature is about 60° C.

Preferably the process according to the second aspect of the present invention provides anhydrous tiotropium bromide with a yield of at least 80% from the starting material (scopine di-(2-thienyl)glycolate), preferably at least 90%, preferably at least 95%, preferably at least 96%, preferably at least 97%, preferably at least 98%.

A third aspect of the present invention provides a process of purifying anhydrous tiotropium bromide, comprising the steps of:
(a) providing a solution of anhydrous tiotropium bromide and an organic solvent;
(b) adding a further organic solvent as an anti-solvent to the solution from step (a);
(c) isolating purified anhydrous tiotropium bromide from the mixture obtained in step (b); and
(d) drying the isolated purified anhydrous tiotropium bromide.

Preferably the organic solvent used in step (a) is a polar aprotic solvent, preferably dimethylsulfoxide, dimethylformamide or dimethylacetamide, preferably dimethylsulfoxide.

Preferably the organic solvent used in step (b) as an anti-solvent is a ketone, preferably acetone, methyl ethyl ketone, methyl n-propyl ketone, methyl isopropyl ketone, methyl vinyl ketone, methyl n-butyl ketone, methyl isobutyl ketone, methyl tert-butyl ketone or diethyl ketone. Preferably the ketone is acetone.

Preferably the drying temperature used in step (d) is between about 40 to 80° C. Preferably the drying temperature is about 60° C.

Preferably the process according to the third aspect of the present invention provides purified anhydrous tiotropium bromide with a yield of at least 80% from the starting material (crude anhydrous tiotropium bromide), preferably at least 90%, preferably at least 95%, preferably at least 96%, preferably at least 97%, preferably at least 98%.

A fourth aspect of the present invention provides anhydrous tiotropium bromide comprising less than 0.5% of impurity scopine di-(2-thienyl)glycolate, preferably less than 0.3%, preferably less than 0.2%, preferably less than 0.1%, preferably less than 0.05%, and most preferably less than 0.03% (as measured by HPLC).

A fifth aspect of the present invention provides anhydrous tiotropium bromide with an HPLC purity of at least 98%, preferably at least 99%, preferably at least 99.5%, preferably at least 99.6%, preferably at least 99.7%, preferably at least 99.8%, preferably at least 99.9%.

Preferably the processes according to the second and third aspects of the present invention provide anhydrous tiotropium bromide according to the first, fourth or fifth aspects of the present invention.

A sixth aspect of the present invention provides anhydrous tiotropium bromide prepared by a process according to the second or third aspect of the present invention. Preferably the anhydrous tiotropium bromide is prepared in a yield of at least 80% from the starting material (scopine di-(2-thienyl)glycolate or tiotropium bromide), preferably at least 90%, preferably at least 95%, preferably at least 96%, preferably at least 97%, preferably at least 98%.

Preferably the anhydrous tiotropium bromide according to the fourth, fifth and sixth aspects of the present invention has an XRPD pattern comprising at least three peaks (preferably at least four peaks, preferably at least five peaks, preferably at least six peaks, preferably at least seven peaks, preferably at least eight peaks, preferably at least nine peaks, preferably at least ten peaks, preferably at least twelve peaks, preferably at least fifteen peaks, preferably at least twenty peaks, preferably all twenty-two peaks) selected from peaks with 2θ angles of about 8.49, 11.38, 13.58, 14.24, 14.74, 16.01, 17.03, 17.93, 18.60, 19.15, 21.80, 22.62, 22.92, 23.29, 25.29, 25.57, 26.23, 27.29, 28.07, 28.61, 30.24 and 31.83±0.2 degrees. Preferably the anhydrous tiotropium bromide according to the fourth, fifth and sixth aspects of the present invention has an XRPD spectrum substantially as shown in FIG. 1.

Preferably the anhydrous tiotropium bromide according to the fourth, fifth and sixth aspects of the present invention has a DSC spectrum with endothermic peaks at about 208° C.±2° C. and about 221° C.±2° C. Preferably the anhydrous tiotropium bromide according to the fourth, fifth and sixth aspects of the present invention has a DSC spectrum substantially as shown in FIG. 2.

Preferably the anhydrous tiotropium bromide according to the fourth, fifth and sixth aspects of the present invention has a TGA spectrum substantially as shown in FIG. 3.

Preferably the anhydrous tiotropium bromide according to the first, fourth and fifth aspects of the present invention is prepared by a process according to the second or third aspect of the present invention.

Preferably the anhydrous tiotropium bromide according to the first, fifth and sixth aspects of the present invention comprises less than 0.5% of impurity scopine di-(2-thienyl)glycolate, preferably less than 0.3%, preferably less than 0.2%, preferably less than 0.1%, preferably less than 0.05%, and most preferably less than 0.03% (as measured by HPLC).

Preferably the anhydrous tiotropium bromide according to the first, fourth and sixth aspects of the present invention has an HPLC purity of at least 98%, preferably at least 99%, preferably at least 99.5%, preferably at least 99.6%, preferably at least 99.7%, preferably at least 99.8%, preferably at least 99.9%.

Preferably the anhydrous tiotropium bromide according to the first, fourth, fifth and sixth aspects of the present invention is suitable for use in medicine, preferably for the treatment of a respiratory disorder. Preferably the respiratory disorder comprises asthma and COPD. Preferably the COPD includes chronic bronchitis and emphysema.

A seventh aspect of the present invention provides a pharmaceutical composition comprising anhydrous tiotropium bromide according to the first, fourth, fifth or sixth aspects of the present invention. Preferably the pharmaceutical composition is suitable for use in a dry powder inhaler (DPI), aqueous nebulizer or a pressurized metered dosage inhaler (pMDI). Preferably the pharmaceutical composition is suitable for the treatment of a respiratory disorder. Preferably the respiratory disorder comprises asthma and COPD. Preferably the COPD includes chronic bronchitis and emphysema.

An eighth aspect of the present invention provides the use of anhydrous tiotropium bromide according to the first, fourth, fifth or sixth aspects of the present invention or the use of the pharmaceutical composition according to the seventh aspect of the present invention, in the manufacture of a medicament for the treatment of a respiratory disorder. Preferably the respiratory disorder comprises asthma and COPD. Preferably the COPD includes chronic bronchitis and emphysema.

A ninth aspect of the present invention provides a method of treating a respiratory disorder, comprising administering to a patient in need thereof a therapeutically effective amount of anhydrous tiotropium bromide according to the first, fourth, fifth or sixth aspects of the present invention or a therapeutically effective amount of the pharmaceutical composition according to the seventh aspect of the present invention. Preferably the respiratory disorder comprises asthma and COPD. Preferably the COPD includes chronic bronchitis and emphysema. Preferably the patient is a mammal, preferably a human.

BRIEF DESCRIPTION OF THE ACCOMPANYING FIGURES

DETAILED DESCRIPTION OF THE INVENTION

The present invention provides a method for preparing anhydrous tiotropium bromide directly from scopine di-(2-thienyl)glycolate without going through tiotropium bromide monohydrate or solvate. Additionally, the present invention provides a method for the purification of anhydrous tiotropium bromide without solvate formation.

Figure 3:
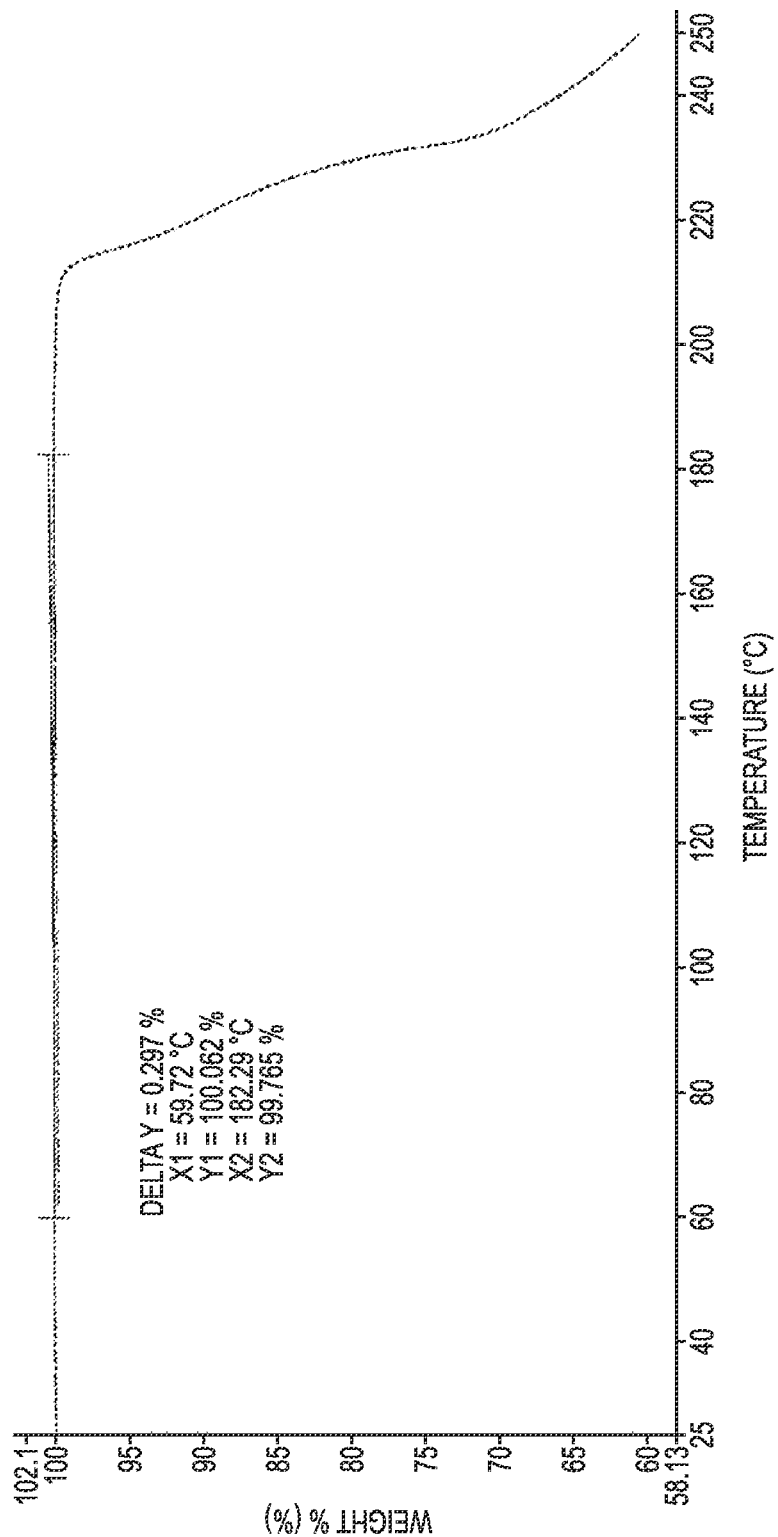
FIG. 3 shows a TGA spectrum of anhydrous tiotropium bromide according to the present invention.

The novel anhydrous form according to the first aspect of the present invention does not contain water of crystallization or solvent of crystallization as shown by the TGA spectrum in FIG. 3.

A preferred process according to the second aspect of the present invention comprises the following steps:
(a) providing a solution of scopine di-(2-thienyl)glycolate and acetone;
(b) adding a solution of methyl bromide in acetonitrile to the mixture from step (a);
(c) isolating anhydrous tiotropium bromide from the mixture obtained in step (b); and
(d) drying the solid.

Preferably, in order to ensure a complete reaction, scopine di-(2-thienyl)glycolate should be fully dissolved in the acetone. Preferably this is achieved by stirring acetone and scopine di-(2-thienyl)glycolate at 25-30° C. High volumes (for example 20 to 50 volumes, preferably about 35 volumes) of acetone may preferably be used to keep the reaction mixture clear to ensure complete conversion.

Preferably, in step (b), a 50% w/w solution of methyl bromide in acetonitrile is employed, preferably at a temperature of 25-30° C. Preferably about 5 volumes of the 50% w/w solution of methyl bromide in acetonitrile are used.

The inventors have also found that stirring the mixture in step (b), preferably for 22 to 26 hours and most preferably for about 24 hours, to facilitate complete conversion is particularly advantageous.

Isolation of the resulting anhydrous tiotropium bromide in step (c) is effected in preferred embodiments by filtration. In further preferred embodiments the isolated anhydrous tiotropium bromide is dried in conditions that do not cause anhydrous tiotropium bromide to degrade. In certain preferred embodiments the anhydrous tiotropium bromide is dried under conditions of reduced pressure, preferably at 55-65° C. Most preferably the anhydrous tiotropium bromide is dried at about 60° C.

The anhydrous tiotropium bromide is very pure, but optionally it can be further purified by the steps of:
(a) providing a solution of anhydrous tiotropium bromide and dimethylsulfoxide;
(b) adding acetone as an anti-solvent to the solution from step (a);
(c) isolating purified anhydrous tiotropium bromide from the mixture obtained in step (b); and
(d) drying the solid.

Preferably the anhydrous tiotropium bromide is dissolved in dimethylsulfoxide at 25-30° C. Preferably about 2 volumes of dimethylsulfoxide are used.

Preferably an anti-solvent, preferably acetone, is added to the above solution to precipitate the solid. Preferably about 20-30 volumes of acetone are used, preferably about 25 volumes.

Isolation of the resulting purified anhydrous tiotropium bromide in step (c) is effected in preferred embodiments by filtration. In further preferred embodiments the isolated purified anhydrous tiotropium bromide is dried in conditions that do not cause anhydrous tiotropium bromide to degrade. In certain preferred embodiments the anhydrous tiotropium bromide is dried under conditions of reduced pressure, preferably at 55-65° C. Most preferably the anhydrous tiotropium bromide is dried at about 60° C.

The polymorphic form of the anhydrous tiotropium bromide does not change during the further purification process.

It has been found that purification of crude anhydrous tiotropium bromide by dissolving in dimethylsulfoxide and precipitating with acetone reduces the level of scopine di-(2-thienyl)glycolate to below 0.1%, preferably less than 0.05%, and most preferably less than 0.03% (as measured by HPLC). The inventors have also found that this particular solvent combination surprisingly does not form a solvate with tiotropium bromide.

According to a further aspect of the present invention there is provided highly polymorphically pure anhydrous tiotropium bromide comprising less than 5% of other polymorphic forms of tiotropium bromide, preferably less than 3%, preferably less than 2%, preferably less than 1%, preferably less than 0.5%, preferably less than 0.2%, and most preferably less than 0.1% of other polymorphic forms of tiotropium bromide (as measured by XRPD).

The crystalline anhydrous tiotropium bromide form in accordance with the invention can be used to advantage in the preparation of pharmaceutical dosage or drug forms. When in particulate form, the crystalline form in accordance with the present invention is stable and free flowing and does not present any of the stability (e.g. polymorphic conversion or chemical conversion) or handling difficulties associated with the prior art forms. The crystalline form according to the invention, therefore, can be employed in the manufacture of pharmaceutical compositions that do not suffer from the problems, such as inconsistent drug substance dissolution rates and the like, that can be manifest in dosage forms manufactured using previously available forms of tiotropium bromide.

The DPI compositions of the present invention preferably contain, in addition to the active substance, the following physiologically acceptable excipients: monosaccharides (e.g. glucose or arabinose), disaccharides (e.g. lactose, sucrose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably mono- or disaccharides are used, while the use of lactose or glucose is preferred, particularly in the form of their hydrates. For the purposes of the present invention, lactose is the particularly preferred excipient, while lactose monohydrate is most particularly preferred.

Preferably the pMDI of the present invention uses HFA 134a, HFA 227 or mixtures thereof as propellant gas.

The pharmaceutical compositions of the present invention preferably contain about 0.001 to 20% tiotropium bromide in admixture with one or more physiologically acceptable excipients. Preferred compositions contain 0.01 to 10% of tiotropium bromide, more preferred are compositions which contain 0.01 to 2% of tiotropium bromide, and most preferred are compositions which contain 0.04 to 0.8% of tiotropium bromide.

The following examples are provided to illustrate the present invention and should not be construed as limiting thereof.

EXAMPLES

As used herein the term "1 volume" or "1 vol" means that for each gram of starting material 1 ml of solvent is used. The terms "2 volumes" or "2 vol" and "3 volumes" or "3 vol" etc. are used accordingly.

Preparation of Anhydrous Tiotropium Bromide from Scopine di-(2-thienyl)glycolate Scopine di-(2-thienyl)glycolate (1 eq) was dissolved in acetone (35 vol) at 25-30° C. and methyl bromide in acetonitrile (50% w/w solution, 5 vol) was added. The mixture was stirred at 25-30° C. for 24 hours and the precipitated solid was filtered and washed with acetone (5 vol). The solid was dried at 60° C. under vacuum to afford the product as a white solid. The crude anhydrous tiotropium bromide obtained was found to have the XRPD, DSC and TGA spectra shown in FIGS. 1, 2 and 3 respectively.

Molar yield=95%
HPLC purity≥99.5-99.7%

Purification of Anhydrous Tiotropium Bromide

Crude anhydrous tiotropium bromide (1 eq) was taken in DMSO (2 vol) and stirred for 1 hour at 25-30° C. Acetone (25 vol) was slowly added and the mixture was chilled to 0-5° C. and stirred at 0-5° C. for 30 minutes. The solid was filtered and washed with acetone (3 vol) and dried under vacuum at 60° C. for 12 hours. The purified anhydrous tiotropium bromide obtained was found to have the XRPD, DSC and TGA spectra shown in FIGS. 1, 2 and 3 respectively.

Molar yield=98%
HPLC purity 99.9%

The crude and purified samples of anhydrous tiotropium bromide prepared in the above examples were found to be substantially pure polymorphically with no levels of other forms detected (>99.7% polymorphically pure, as measured by XRPD). The purified anhydrous tiotropium bromide prepared was also found to be very stable chemically and polymorphically with no conversion over time to other polymorphs. The stability of the sample was tested by subjecting the sample to accelerated stability conditions (40° C.±2° C. temperature and 75%±5% relative humidity) for 6 months. The chemical purity (measured by related substances and purity assays by HPLC) and polymorphic purity (measured by XRPD, DSC and TGA) were monitored for 6 months and the sample was found to be chemically and polymorphically stable even after 6 months under accelerated stability conditions.

The XRPDs were recorded on a Bruker D8 Advance Diffractometer, using Cu Kα1 radiation as the X-ray source and LynxEye as the detector, with a 2θ range of from 3° to 50°, a step-size of 0.05° and a time/step of 1 sec.

The DSCs were recorded on a Perkin Elmer Pyris 6 Instrument over a temperature range of from 25° C. to 250° C. at a rate of heating of 10° C./min.

The TGAs were recorded on a Perkin Elmer Pyris 1 Instrument over a temperature range of from 25° C. to 250° C. at a rate of heating of 10° C./min.

It will be understood that the present invention has been described above by way of example only. The examples are not intended to limit the scope of the invention. Various modifications and embodiments can be made without departing from the scope and spirit of the invention, which is defined by the following claims only.

Figure 1:
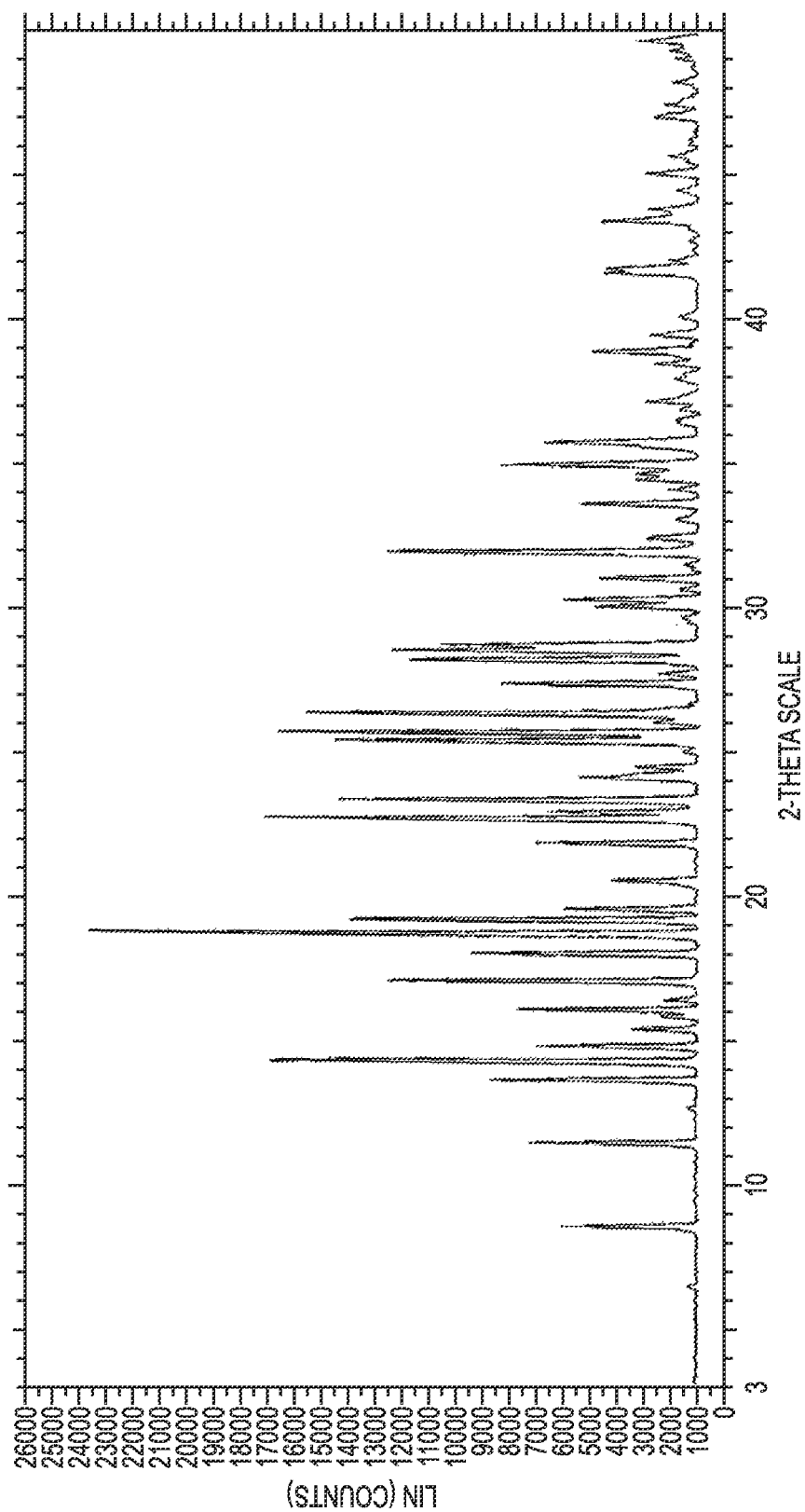
FIG. 1 shows an XRPD spectrum of anhydrous tiotropium bromide according to the present invention.
Figure 2:
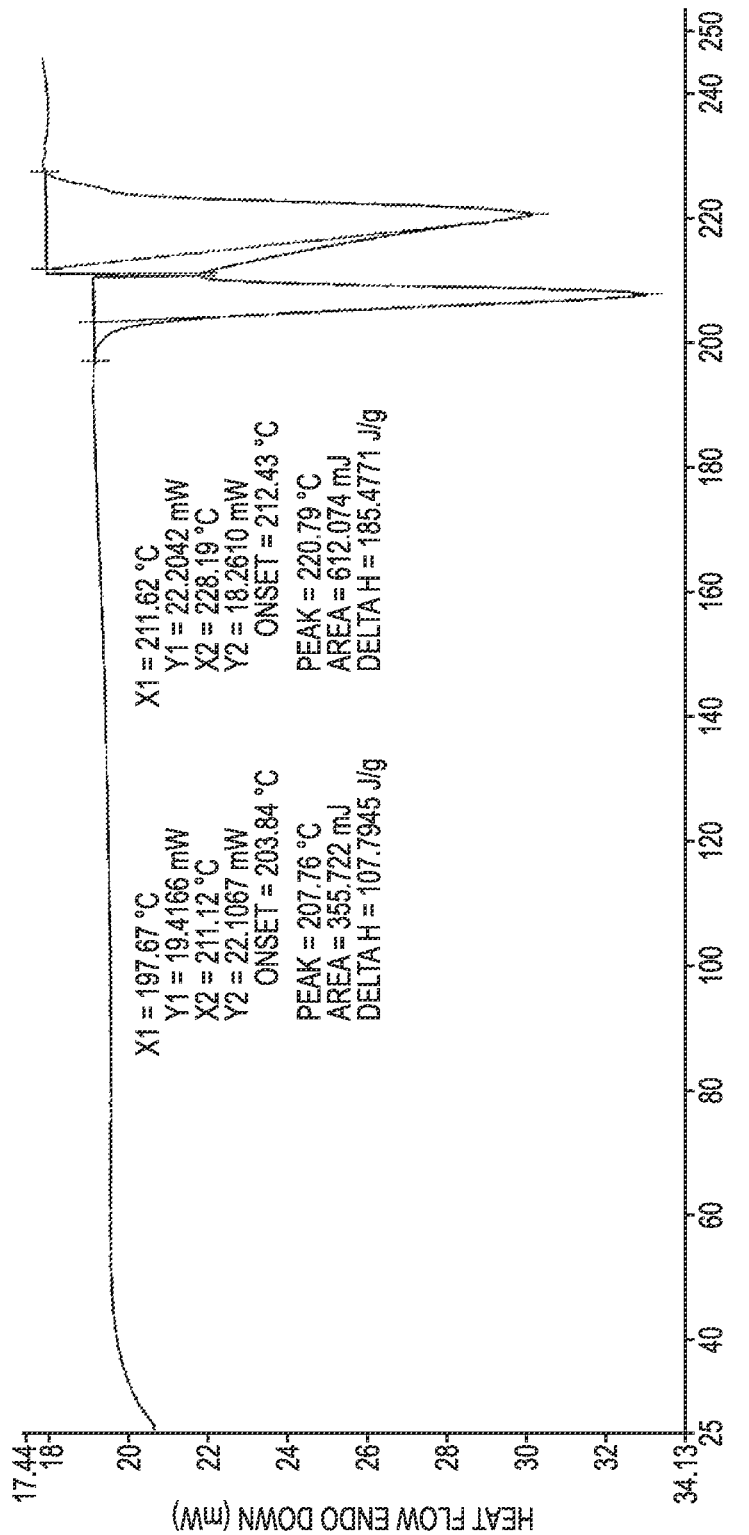
FIG. 2 shows a DSC spectrum of anhydrous tiotropium bromide according to the present invention.

The invention claimed is:

1. A process for the preparation of anhydrous tiotropium bromide having an XRPD pattern comprising at least three peaks selected from peaks with 2θ angles of about 8.49, 11.38, 13.58, 14.24, 14.74, 16.01, 17.03, 17.93, 18.60, 19.15, 21.80, 22.62, 22.92, 23.29, 25.29, 25.57, 26.23, 27.29, 28.07, 28.61, 30.24 and 31.83±0.2 degrees, wherein the anhydrous tiotropium bromide further comprises:
  (i) an XRPD spectrum substantially as shown in FIG. 1; and/or
  (ii) a DSC spectrum with endothermic peaks at about 208° C.+2° C. and about 221° C.+2° C.; and/or
  (iii) a DSC spectrum substantially as shown in FIG. 2; and/or
  (iv) a TGA spectrum substantially as shown in FIG. 3;
wherein the process comprises the steps of:
  (a) providing a solution of scopine di-(2-thienyl)glycolate and a first organic solvent;
  (b) adding a solution of methyl bromide in a second organic solvent to the mixture from step (a) or vice versa;
  (c) isolating anhydrous tiotropium bromide from the mixture obtained in step (b); and
  (d) drying the isolated anhydrous tiotropium bromide.

2. A process according to claim 1, wherein:
  (i) the first organic solvent is a ketone such as acetone; and/or
  (ii) the second organic solvent is acetonitrile; and/or
  (iii) the drying temperature is between about 40 to 80° C. or is about 60° C.

3. A process according to claim 1, comprising an additional process for further purifying the anhydrous tiotropium bromide.

4. A process according to claim 3, wherein the additional process for further purifying the anhydrous tiotropium bromide comprises:
  (a) providing a solution of anhydrous tiotropium bromide and a third organic solvent;
  (b) adding a fourth organic solvent as an anti-solvent to the solution from step (a);
  (c) isolating purified anhydrous tiotropium bromide from the mixture obtained in step (b); and
  (d) drying the isolated purified anhydrous tiotropium bromide.

5. A process according to claim 4, wherein:
  (i) the third organic solvent is dimethylsulfoxide; and/or
  (ii) the fourth organic solvent used as an anti-solvent is a ketone such as acetone; and/or
  (iii) the drying temperature is between about 40 to 80° C. or is about 60° C.

* * * * *